US009334316B2

(12) United States Patent
Ward et al.

(10) Patent No.: US 9,334,316 B2
(45) Date of Patent: May 10, 2016

(54) FORMULATIONS COMPRISING GLUCAGON

(71) Applicants: W. Kenneth Ward, Portland, OR (US); Jessica R. Castle, Portland, OR (US); Nicholas Caputo, Portland, OR (US); Parkash A. Bakhtiani, Portland, OR (US)

(72) Inventors: W. Kenneth Ward, Portland, OR (US); Jessica R. Castle, Portland, OR (US); Nicholas Caputo, Portland, OR (US); Parkash A. Bakhtiani, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 0 days.

(21) Appl. No.: 14/682,721

(22) Filed: Apr. 9, 2015

(65) Prior Publication Data

US 2015/0291680 A1 Oct. 15, 2015

Related U.S. Application Data

(60) Provisional application No. 61/978,334, filed on Apr. 11, 2014.

(51) Int. Cl.
*C07K 14/605* (2006.01)
*A61K 38/00* (2006.01)

(52) U.S. Cl.
CPC ............... *C07K 14/605* (2013.01); *A61K 38/00* (2013.01)

(58) Field of Classification Search
None
See application file for complete search history.

(56) References Cited

U.S. PATENT DOCUMENTS

2007/0243132 A1* 10/2007 Russell-Jones ...... A61K 9/0014 424/1.11

* cited by examiner

*Primary Examiner* — Thomas S Heard
(74) *Attorney, Agent, or Firm* — Jeffrey M. Jackson

(57) ABSTRACT

Glucagon formulations that resist fibril formation are disclosed. The formulations comprise curcumin derivatives such as ferulic acid and/or tetrahydrocurcumin and can further comprise human serum albumin, polysorbate-80, and L-methionine.

12 Claims, 8 Drawing Sheets

FORMULATIONS COMPRISING GLUCAGON

FIELD

Generally, the field of the invention includes formulations used in the treatment of hypoglycemia. More specifically, the field includes formulations comprising glucagon that provide enhanced glucagon stability in solution.

BACKGROUND

Glucagon is very useful in type 1 diabetes, both as a rescue drug given in large doses to persons who have severe hypoglycemia, and in small doses in the setting of automatic closed loop glycemic management. In solution, glucagon is highly unstable, and must be reconstituted often for the closed loop application.

In the 1950's, after its purification and crystallization, glucagon was also found to form many slender fibrillar structures in solution (Staub A and Behrens O K, *J Clin Invest* 33, 1629-1633 (1954), incorporated by reference herein). This fibrillation increases with incubation time; further aging of glucagon solutions leads to gels with high concentrations of packed fibrils. The fibrils have a beta-pleated sheet amyloid protein configuration. Though some compounds, including cyclodextrins, have been reported to reduce the tendency to form these fibrils (Matilainen L et al, *J Pharm Sci* 97, 2720-2729 (2007 and Matilainen L et al, *Eur J Pharm Sci* 36, 412-420 (2008) both of which are incorporated by reference herein) there is no additive or method that is known to block their formation. In 2004, fibrillated glucagon was reported to be cytotoxic in cultured mammalian cells (Onoue S et al, *Pharm Res* 21, 1274-1283 (2004), incorporated by reference herein). The authors emphasized the potentially dangerous nature of these fibrils and pointed out the presence of similar fibrils in Alzheimer's-, Parkinson's- and prion diseases.

First mentioned in 1964 (Kadish A, *Am J Med Electron* 3, 82-86 (1964) incorporated by reference herein,) there has been a resurgence of interest in the automated delivery of glucagon during frequent glucose measurement in order to prevent hypoglycemia in people with type 1 diabetes. In the closed loop setting, several reports showed benefit of glucagon administration in animals (El-Khatib F H et al, *J Diabetes Sci Technol* 3, 789-803 (2009) and Ward W et al, *IEEE Sensors Journal* 8, 88-96 (2008), both of which are incorporated by reference herein) and in humans (Castle J R et al, *Diabetes Care* 33, 1282-1287 (2010) and El-Khatib F G et al *Sci Transl Med* 2, 27ra27 (2010), both of which are incorporated by reference herein). In the Castle (2010) reference supra, the duration of time in the hypoglycemic range for a bihormonal approach including both glucagon and insulin was less than half the duration for the insulin-only experiments. The doses of subcutaneous glucagon in closed loop studies are generally small, and range from 30-180 μg. To perform these studies, the glucagon must be frequently reconstituted to minimize fibril formation. Frequent reconstitution is not a viable option for treating patients.

Glucagon is readily soluble in alkaline conditions (around pH 10) and at 37° C., there is much less amyloid fibril formation in glucagon solubilized under alkaline conditions than compared to glucagon solubilized under the acidic conditions (about pH 3) commonly used in currently available commercial preparations of glucagon (Ward W K et al, *J Diabetes Sci Technol* 4, 1311-1321 (2010), incorporated by reference herein). Glucagon aged for 5 days at a pH of 8.5 showed some cytotoxicity at pH 8.5 at a concentration of 2.5 mg/ml. Glucagon aged at pH 10 in glycine, showed no cytotoxicity. However, glucagon solubilized at alkaline conditions spontaneously degrades.

Therefore, what is clearly needed is a stable glucagon formulation that inhibits fibril formation and resists glucagon degradation for at least three days and preferably seven days so that the glucagon formulation may be administered in a pump.

Curcumin reduces Aβ fibril formation in vitro and when administered systemically to transgenic rodents predisposed to Alzheimer's disease (Hamaguchi T et al, *Am J Pathol* 175, 2557-2565 (2009) incorporated by reference herein). Curcumin has also been reported to inhibit the polymerization of α-synuclein, the compound responsible for Lewy body formation in diseases such as Parkinson's disease (Ono K and Yamada M, *Curr Pharm Des* 14, 3247-3266 (2008) and Ono K et al *Curr Pharm Des* 14, 3247-3266 (2008); both of which are incorporated by reference herein). This finding was confirmed in Pandey N et al, *Acta Neuropathol* 115, 479-489 (2008); which is incorporated by reference herein. However, curcumin stored in a glycine buffer at pH 9.0 degrades quickly with a half-life of about 7 hours. While this half-life could be extended to 12.5 hours in a glucagon buffer and further to 33.5 hours with the further addition of human serum albumin, this is not a sufficiently stable for the purposes of an automated delivery system.

SUMMARY

Disclosed herein are formulations comprising glucagon as well as curcumin derivatives, particularly ferulic acid and tetrahydrocurcumin. These formulations reduce fibrillation and do not excessively oxidize the glucagon. In addition, the formulations can further comprise a buffer at a pH of between 8.8 and 9.4. The formulation can comprise any amount of glucagon, including 1 mg/ml. The buffer may be any buffer, including a glycine buffer, including an 80 mM glycine buffer. The buffer can further comprise other excipients such as polysorbate 80 and albumin, including human serum albumin. The buffer can further comprise L-methionine including at least 0.1 mg/ml L-methionine if the formulation comprises ferulic acid and at least 1 mg/ml L-methionine if the formulation comprises tetrahydrocurcumin.

BRIEF DESCRIPTION OF THE DRAWINGS

Some of the drawings in this disclosure are photographic images that may not reproduce properly in a patent application publication. Additionally, some of the drawings may be better understood when viewed in color, which is not available in a patent application publication. Applicants consider all photographic images and color drawings as part of the original disclosure and reserve the right to present high quality and/or color images of the herein described figures in later proceedings.

$$\text{Potency shift} = \frac{(7\text{ day } EC_{50} - 0\text{ day } EC_{50})}{0\text{ day } EC_{50}}$$

Figure 7:
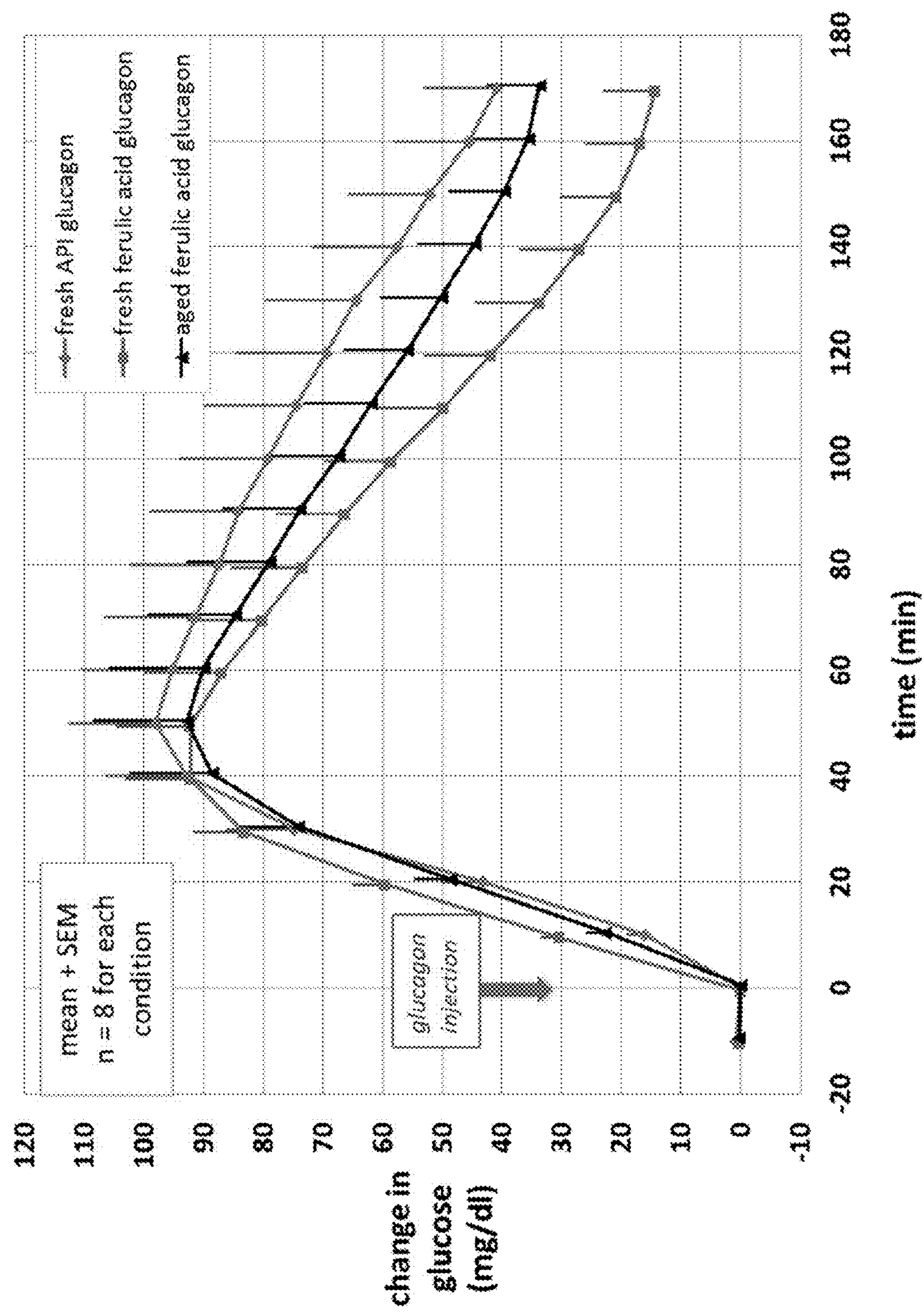

FIG. 7 is a line plot showing the results of a study in which 8 pigs each were given fresh FAFG, FAFG (aged×7 days at 37° C.) and fresh buffered glucagon without excipients. Animals were anesthetized with isoflurane. The animals were injected with glucagon at time 0 and glucose was monitored as indicated on the X axis.

DETAILED DESCRIPTION

Disclosed herein are formulations comprising glucagon that preserve the stability of glucagon in solution under physiological conditions for extended periods of time without the formation of fibrils.

The formulations comprise one or more of ferulic acid and/or tetrahydrocurcumin. The parent molecule for both ferulic acid and tetrahydrocurcumin is the polyaromatic compound curcumin. Curcumin has gained attention recently due to its ability to inhibit amyloid formation in neurodegenerative diseases. Ferulic acid is essentially one-half of a curcumin molecule and tetrahydrocurcumin is the reduced form of curcumin. Curcumin is found naturally in the rhizome of *Curcuma longa,* more commonly known as turmeric (Anand P et al, *Biochem Pharmacol* 76, 1590-1611 (2008); incorporated by reference herein). It is responsible for the orange pigmentation of the root and indeed, when in solution there is a deep orange color. Tetrahydrocurcumin is believed to be one of the ultimate metabolites of curcumin in the plasma (Pan MH et al, *Drug Metab Dispos* 27, 486-494 (1999); incorporated by reference herein). Tetrahydrocurcumin pharmacology has also been tested extensively, as reviewed extensively in Anand et al 2008 supra, and has been shown to have beneficial effects for antioxidant activity, hepatotoxicity, lipid peroxidation, hypertension, aortic stiffening, and positive diabetes effects to name a few. Ferulic acid has been shown to be a breakdown product of curcumin along with vanillic acid (Wang Y J et al, *J Pharm Biomed Anal* 15, 1867-1876 (1997) incorporated by reference herein). It is naturally found in plant cell walls as well as in the seeds and leaves. It is also an abundant metabolite of phenylalanine and tyrosine degradation via the shikimate pathway. Foods rich in ferulic acid include brown rice, whole wheat, and oats. Other good sources of ferulic acid are coffee, amaranth, artichokes, peanuts, oranges, pineapple, and apples. It has been shown to have antioxidant properties, protective effect on bone loss, positive lipid effects, and have positive effects on diabetes. It is currently finding use in cosmetics like skin lighteners, sunscreens, anti-aging creams, and moisturizers and is approved for use as a food additive in Japan (Gohil et al, *Int J Pharm Sci Res* 3, 700-710 (2012); and Wang B H et al, *Cardio Drug Rev* 23, 161-172 (2005); both of which are incorporated by reference herein).

The glucagon formulation is provided and administered in a buffer. Appropriate buffers are those that maintain the mixture at a pH range from about 8.8 to about 10.0. Examples of appropriate buffers include, but are not limited to, EPPS, Tricine, glycine (gly-gly) bicine, HEPBS, TAPS, AMPD, TABS, AMPSO, CHES, CAPSO, AMP, CAPS, CABS, and any other buffers that maintain a solution in a pH range of about 8.8 to about 10.0. The selection of appropriate buffers will be well understood by one of one of ordinary skill in the art in light of this disclosure.

Glucagon is administered in order to prevent hypoglycemia. Prevention of hypoglycemia is achieved through maintaining an average blood glucose level of a subject above about 70 mg/dL, or above about 50-60 mg/dL. Most preferably, the subject's blood glucose level is maintained so that normoglycemia is maintained, without the onset of hyperglycemia.

Glucagon can elevate blood glucose above where it would be without the administration of exogenous glucagon. Preferably, the dose administered is one that is still protective against hypoglycemia but only minimally elevates blood glucose above the levels maintained in the patient when not suffering from hypoglycemia.

The control of hypoglycemia by glucagon therapy, can involve parenteral administration of the insulin or glucagon. Parenteral administration may be performed by subcutaneous or intramuscular injection using a syringe, such as a hypodermic syringe or pen-type syringe, pump, or closed loop system.

In one example, a pump system is used to provide a prolonged release of glucagon. Pump systems that may be used to administer the glucagon include syringe pumps, peristaltic pumps, contraction pumps, and the like.

Glucagon with a low activity level is desirable in some circumstances. As the delivery of precise amounts of small volumes can be difficult, especially over prolonged periods of time, compositions of glucagon comprising components that lower the activity of glucagon may be desirable in some situations to allow the administration of larger volumes of sample. Alternatively, variants or mutants of glucagon with a lower activity level can be used to achieve this result. The term "glucagon" can encompass both wild-type glucagon and variants or derivatives of glucagon.

In one embodiment, parenteral administration of the glucagon formulation is performed through the use of an infusion pump. A variety of pumps are available and in common use that are suitable for delivery of insulin and the glucagon formulation (as well as suitable for the delivery of insulin, with glucagon being delivered by another route, such as transdermal). The glucagon can optionally be administered in combination with insulin, and a glucagon with a short duration of action can be employed, as the glucagon can be administered as necessary.

In another alternative, the glucagon may be administered via an automatic pump system, while the insulin is administered via an open loop system (via a pump or with insulin injections.)

The glucagon formulation may be administered via a pump suitable for the delivery of insulin for the control of diabetes, and for the delivery of glucagon for the control of hypoglycemia in a human, i.e., the pump contains both insulin and glucagon. In other embodiments, the pump includes insulin and glucagon in two separately controlled reservoirs.

The glucagon formulation can be provided as a liquid suitable for administration as a nasal or pulmonary spray. A variety of such formulations are known and one of skill in the art in light of this disclosure will understand how to prepare such formulations.

The glucagon formulation can be provided in a formulation suitable for transdermal administration, such as from a patch, or transmucosally, e.g. bucally. Manufacture and use of transdermal delivery devices are well known in the art and one of skill in the art in light of this disclosure will understand how to prepare such formulations.

The glucagon formulation described herein can be provided in a kit. In one embodiment, the kit comprises a vial of the glucagon formulation, a device used in administration, such as a syringe or pump, and instructions that describe the administration of the glucagon formulation. The kit can also comprise a vial of insulin. The particular instructions will vary depending upon the desired use of the kit, e.g. for emergency control of hypoglycemia or otherwise. The instructions can be determined by one of skill in the art, in light of the present disclosure and the particular use intended for the kit. In one embodiment, the instructions will describe all or part of the methods disclosed herein.

Administration of low doses of glucagon can be inconvenient using formulations prepared according to conventional methods (e.g., resulting in an approximately 1 mg/ml solution). In various embodiments, glucagon is administered as a solution having a concentration of less than about 0.25 mg/ml, for example, less than about 0.2 mg/ml, less than about 0.1 mg/ml, less than about 0.05 mg/ml, less than about 0.01 mg/ml, or even less than about 0.005 mg/ml of glucagon. Such amounts can be appropriate for IV administration and dose equivalent amounts can be created for other methods of administration. For example, if the method of administration is subcutaneous administration, then the concentration of glucagon can be higher, at least about 0.1 mg/ml, or 0.3 mg/ml, or 0.5 mg/ml, or between about 0.5 mg/ml and 2 mg/ml or between 2 mg/ml and 5 mg/ml or 5 mg/ml of glucagon or more. In some embodiments, these doses are combined with a device that can administer the doses in low amounts over a prolonged period of time, such as a pump.

Formulations that enhance the stability of glucagon in solution comprise glucagon in a buffer in addition to one or more excipients that stabilize the glucagon from deamidation or other degradation and/or prevent the formation of amyloid fibrils. there are other compounds that stabilize glucagon and prevent either the degradation or fibrillation: Examples of excipients include lactose at a concentration of between 1-100 mg/ml, between 2-50 mg/ml, 5-20 mg/ml, or between 8-12 mg/ml; albumin at a concentration of between 0.5-50 mg/ml, 0.5-20 mg/ml, 0.8-5 mg/ml, and 0.8-2 mg/ml; glycerol from 5-50% w/v; polyvinyl pyrollidone, AKA PVP or povidone from 2-20% w/w; curcumin from 0.1 mM to 2 mM; or trehalose at 0.1-0.5 molar, either alone or in combination with any other listed excipient or any other ingredient in the formulation.

Additional additives may include antioxidants such as sulfites, bisulfites, and methionine as well as antimicrobials such as m-cresol or phenol.

Formulations of glucagon with enhanced stability in solution are particularly useful in combination with a device that is intended to treat hypoglycemia in an emergency situation. Currently, in an emergency, glucagon provided in a lyophilized or other powdered state must be mixed with water or another liquid. A person with diabetes undergoing a hypoglycemic event may have difficulty in mixing the powder with the liquid. The formulation of glucagon with enhanced stability in solution could be provided in a pen-type syringe to be administered by the person with diabetes or a caregiver or other person.

EXAMPLES

The following examples are illustrative of disclosed compositions. In light of this disclosure, those of skill in the art will recognize that variations of these examples and other examples of the disclosed compositions would be possible without undue experimentation.

Example 1

Glucagon Formulations

Examples of glucagon formulations, including those used in the Examples below are summarized in Table 1.

TABLE 1

Glucagon formulations - HSA = human serum albumin, FA = ferulic acid, THC = tetrahydrocurcumin, L-met = L-methionine, and P-80 = polysorbate 80

| Glucagon (mg/ml) | Glycine (mM) | pH | HSA (mg/ml) | FA (mM) | THC (mM) | L-met (mg/ml) | P-80 (% v/v) |
|---|---|---|---|---|---|---|---|
| 1.0 | 80.0 | 9.0 | — | — | — | — | —[a] |
| 1.0 | 80.0 | 9.0 | — | 1.0 | — | — | — |
| 1.0 | 80.0 | 9.0 | — | — | 1.0 | — | — |
| 1.0 | 80.0 | 9.0 | 1.0 | — | — | — | —[d] |
| 1.0 | 80.0 | 9.0 | 1.0 | 1.0 | — | — | — |
| 1.0 | 80.0 | 9.0 | 1.0 | — | 1.0 | — | — |
| 1.0 | 80.0 | 9.0 | 1.0 | 1.0 | — | 0.1 | — |
| 1.0 | 80.0 | 9.0 | 1.0 | 1.0 | — | 1.0 | — |
| 1.0 | 80.0 | 9.0 | 1.0 | — | 1.0 | 0.1 | — |
| 1.0 | 80.0 | 9.0 | 1.0 | — | 1.0 | 1.0 | — |
| 1.0 | 80.0 | 9.0 | 1.0 | 1.0 | — | 0.1 | 0.5[b] |
| 1.0 | 80.0 | 9.0 | 1.0 | — | 1.0 | 1.0 | 0.5[c] |

Figure 3:
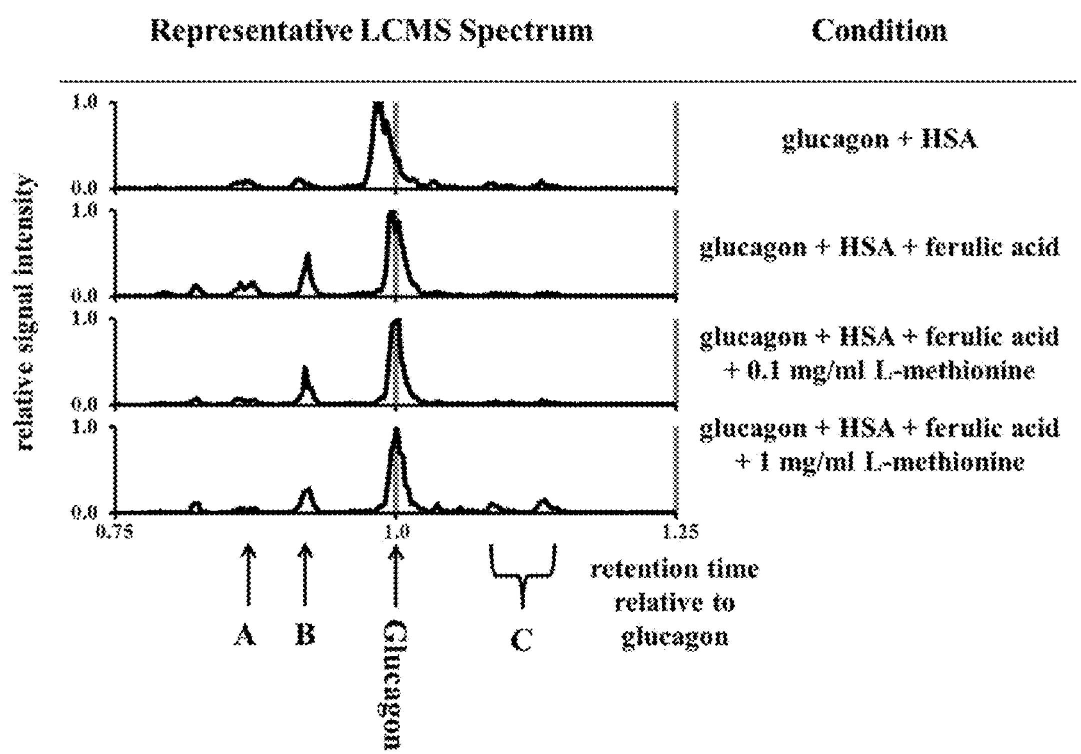
FIG. 3 is a set of four chromatograms from reversed phase LCMS showing the modifications present in glucagon incubated with ferulic acid under the indicated conditions and the recovery by adding varying amounts of L-methionine. The peak indicated as 'A' is identified as Met27 oxidation of glucagon; the peak indicated as 'B' is a minor breakdown product; the peaks indicated as 'C' are identified as glycine adducts.
Figure 4:
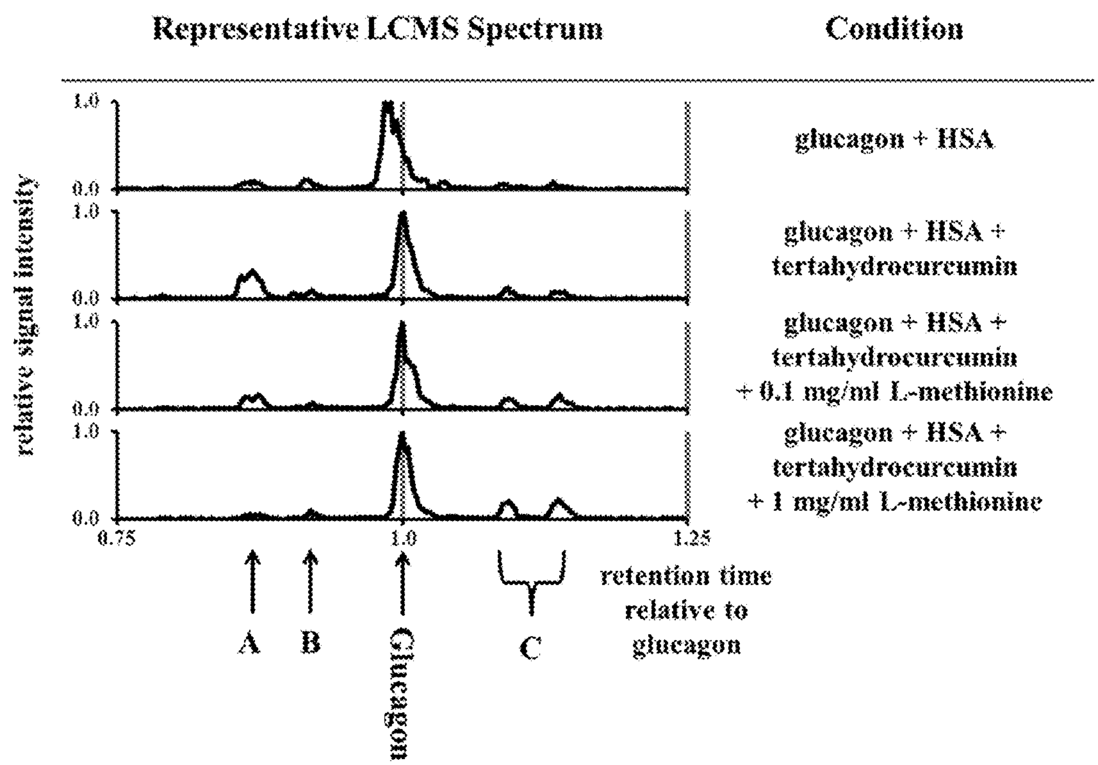
FIG. 4 is a set of four spectra from reversed phase LCMS showing the modifications present in glucagon incubated under the indicated conditions. The peak indicated as 'A' is identified as Met27 oxidation of glucagon; the peak indicated as 'B' is a minor breakdown product; the peaks indicated as 'C' are identified as glycine adducts.

[a]this formulation is referred to as BG herein.
[b]this formulation is referred to as FAFG herein.
[c]this formulation is referred to as TCHFG herein.
[d]formulation is used in FIGS. 3 and 4.

Example 2

Glucagon Formulations Comprising Ferulic Acid

Table 2 shows that 1 mM ferulic acid (FA) in a formulation comprising 80 mM glycine at pH 9.0 alone, in a formulation comprising 1 mg/ml glucagon, or in a formulation with 1 mg/ml glucagon+1 mg/ml human serum albumin is completely stable with no measurable degradation half-life able to be determined over the time course measured. Therefore ferulic acid displays long term stability at pH 9.0 in a glucagon formulation and is not affected by the presence of other factors within the solution such as human serum albumin.

Ferulic Acid Structure:

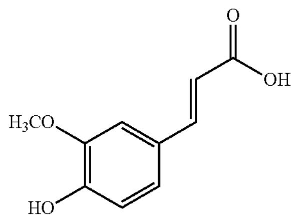 [SMILES: COc1cc(/C=C/C(=O)O)ccc1O]

TABLE 2

| Degradation kinetics of ferulic acid in glucagon formulations | | |
|---|---|---|
| | $1^{st}$ Order Degradation Kinetics | |
| Formulation: | k (/s) | $t_{1/2}$ (hours) |
| 1 mM ferulic acid + 80 mM glycine pH 9.0 | $-7.01 \times 10^{-4}$ | No degradation detected |
| 80 mM glycine pH 9.0 + 1 mg/ml glucagon | $-3.64 \times 10^{-5}$ | No degradation detected |
| 80 mM glycine pH 9.0 + 1 mg/ml glucagon + 1 mg/ml HSA | $1.05 \times 10^{-5}$ | 66,007.43 |

Example 3

Glucagon Formulations Comprising Tetrahydrocurcumin

Table 3 shows that when 1 mM tetrahydrocurcumin is incubated at pH 9.0 in 80 mM glycine, it has a half-life on the order of about 78 hours, showing linear 1st order kinetic fitting. In a composition comprising tetrahydrocurcumin and 1 mg/ml glucagon, the tetrahydrocurcumin half-life rises to 933 hours and when 1 mg/ml HSA is further added, the half-life becomes unmeasurable over the scope of this experiment.

Tetrahydrocurcumin Structure:

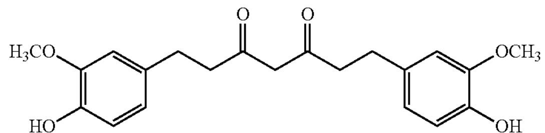 [SMILES: COc1cc(CCC(=O)CC(=O)CCc2ccc(O)c(OC)c2)ccc1O]

TABLE 3

| | $1^{st}$ Order Degradation Kinetics | |
|---|---|---|
| Formulation: | k (/s) | $t_{1/2}$ (hours) |
| 1 mM tetrahydrocurcumin + 80 mM glycine pH 9.0 | $8.86 \times 10^{-3}$ | 78.26 |
| 80 mM glycine pH 9.0 + 1 mg/ml glucagon | $7.43 \times 10^{-4}$ | 933.02 |
| 80 mM glycine pH 9.0 + 1 mg/ml glucagon + 1 mg/ml HSA | $-2.50 \times 10^{-3}$ | No degradation detected |

Example 4

Figure 1:
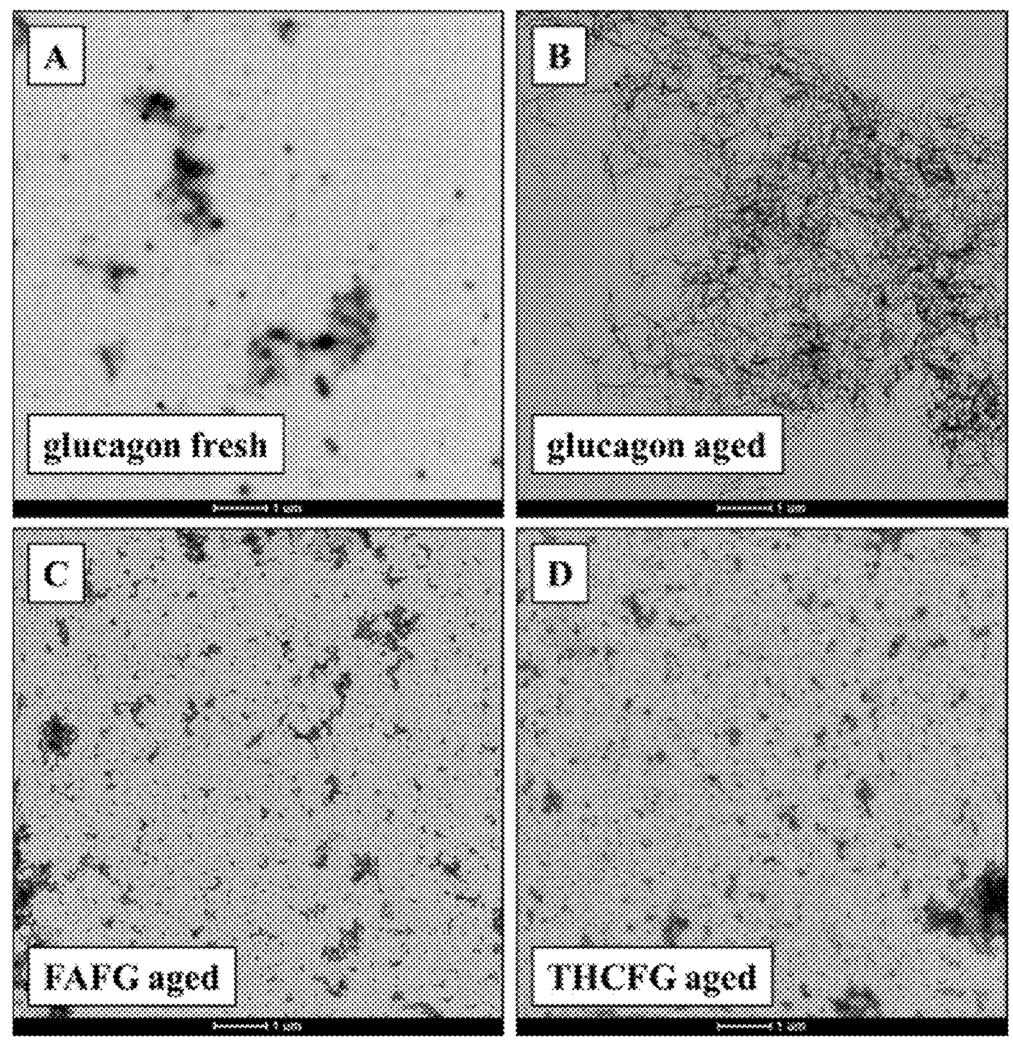
FIG. 1 is a set of four representative transmission electron micrographs (4,800× magnification) (labeled A-D on the figure) comparing (A) fresh buffered glucagon (BG) (1 mg/ml in 80 mM glycine pH 9) with: (B) BG aged 7 days at 37° C. (C) glucagon aged 7 days at 37° C. in FAFG (1 mg/ml in 80 mM glycine pH 9.0+1 mg/ml human serum albumin (HSA)+0.5% (v/v) polysorbate 80+0.1 mg/ml L-methionine+1 mM ferulic acid) (D) buffered glucagon aged 7 days at 37° C. in THCFC (1 mg/ml in 80 mM glycine pH 9.0+1 mg/ml HSA+0.5% polysorbate 80+1 mg/ml L-methionine+1 mM tetrahydrocurcumin)

Formulations Comprising Ferulic Acid and Tetrahydrocurcumin Inhibit Glucagon Peptide Aggregation FIG. 1 is a set of transmission electron micrographs intended to show formation of fibrils in a set of different formulations. Image A is fresh glucagon in BG. Image B is glucagon aged 7 days in BG. Image C is 1 mg/ml glucagon aged 7 days in FAFC. Image D is 1 mg/ml glucagon aged 7 days THCFC. The images in FIG. 1 are representative of 120 images per condition. Fibrils were detected in all 120 images of the 7 day aged glucagon in BG by three different observers. No fibrils were seen in any of the 120 images of fresh glucagon in BG or in the 7 day aged FAFC or THCFC formulations.

Figure 2:
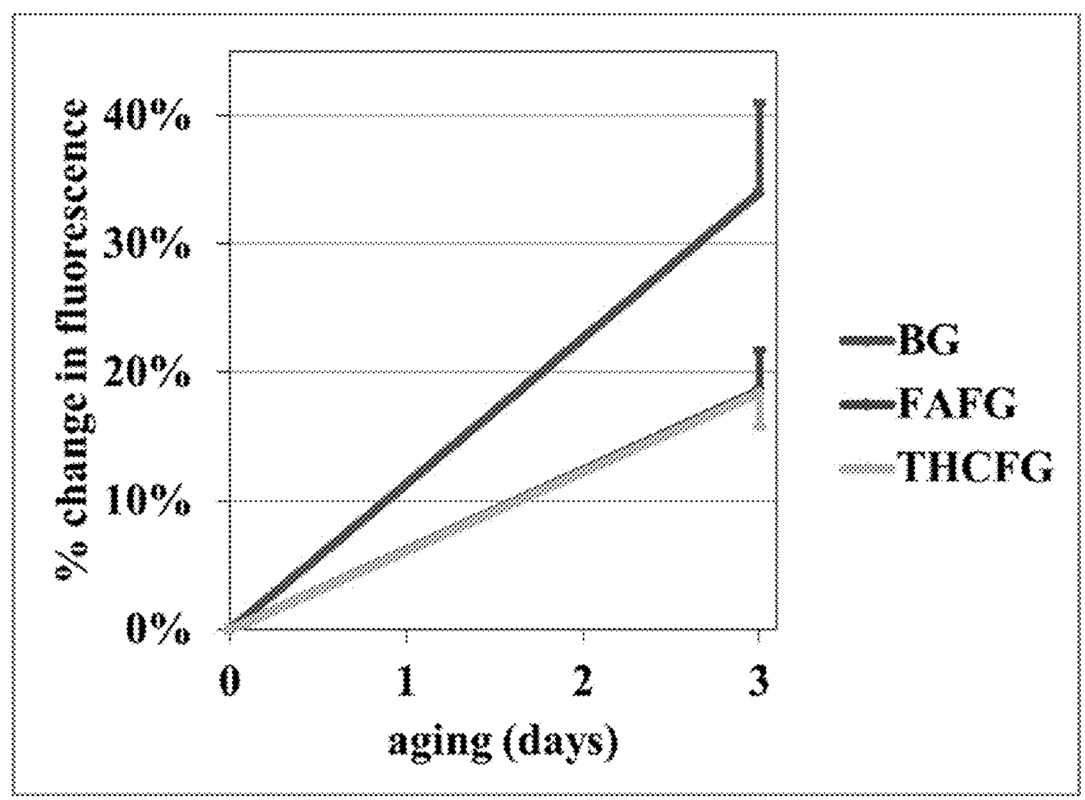
FIG. 2 is a plot of thioflavin T fluorescence of BG vs. FAFG and THCFC all formulated as described above against the time of incubation.

FIG. 2 is a chart showing the results of an assay using Thioflavin T, a fluorescent probe that detects fibrillation. Thioflavin T was added to glucagon formulated as indicated. Glucagon in the BG formulation rapidly fibrillates after three days. Glucagon in the FAFG or THFC formulations show reduced fibrillation.

Example 5

Oxidation of Glucagon After Aging in the Presence of Ferulic Acid or Tetrahydrocurcumin is Inhibited by L-methionine When glucagon is aged for 7 days at 37° C. with 1 mM ferulic acid, minor oxidation occurs, as seen in peak A, most visible in the second LCMS spectrum (from the top of the figure) in FIG. 3. This oxidation occurs on amino acid residue 27, which is a methionine residue (Met27). In order to minimize oxidation, L-methionine was added to the formulation as an antioxidant at 0.1 and 1 mg/ml. As shown in the bottom panel of FIG. 3, the addition of 1 mg/ml L-methionine resulted in the minimization of oxidation (peak A) but also resulted in the formation of several glycine adducts (peaks C). This is presumably due to activation of a reactive site on the glucagon backbone that results in an addition reaction with glycine from the bulk solvent. In order to maximize the antioxidant properties while also minimizing the glycine adduct formation, a concentration of 0.1 mg/ml L-methionine was tested. Results are shown in the third panel from the top of FIG. 3. This particular formulation had some minor chain cleavage (peak B) that is variable from batch to batch. As a result, the formulation referred to herein as FAFG includes 0.1 mg/ml L-methionine.

Similar to FIG. 3, FIG. 4 shows that incubation of glucagon with tetrahydrocurcumin results in a much higher amount of Met27 oxidation, as seen in peak A in the second panel of FIG. 4. This peak is inhibited at 0.1 mg/ml L-methionine added and nearly absent at 1 mg/ml L-methionine to minimize the oxidation even though glycine adducts are still in high amounts. As a result, the formulation referred to herein as THCFG includes 1 mg/ml L-methionine.

Example 6

Glucagon Parent Peak Retention via HPLC

Figure 5:
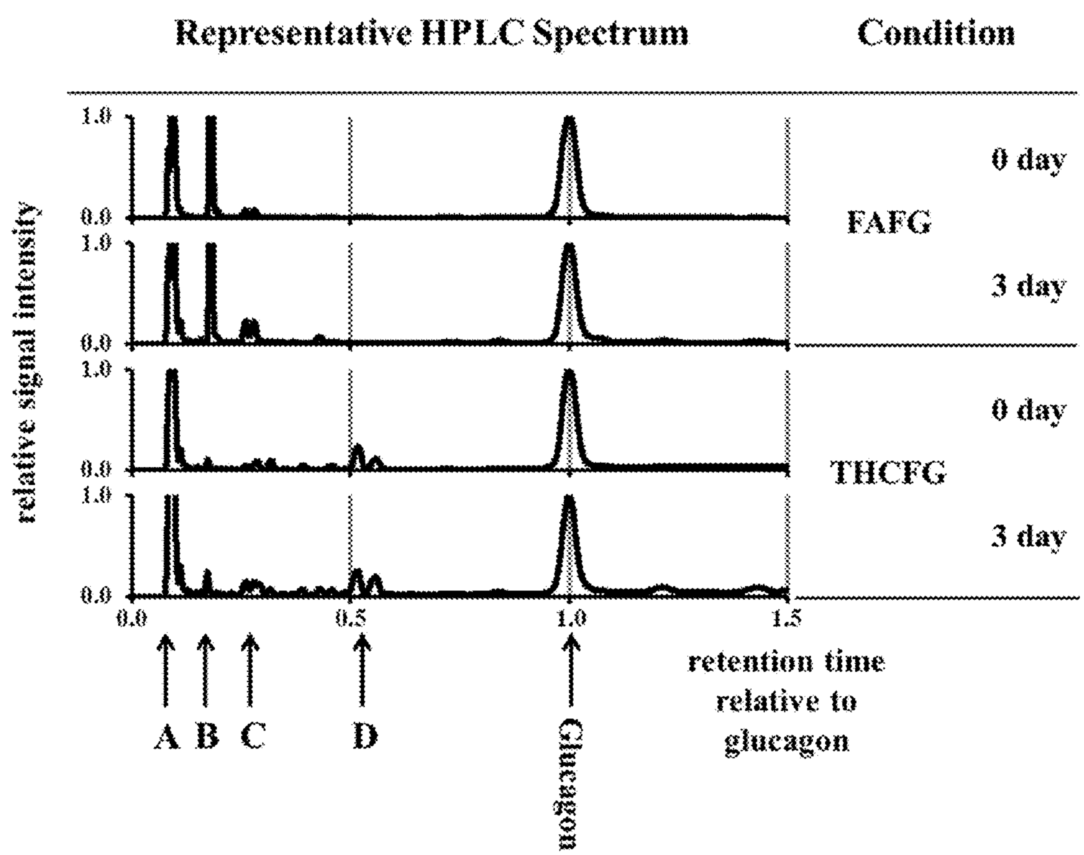
FIG. 5 is a set of four spectra from high-pressure liquid chromatography according to United States Pharmacopeial methods depicting retention times of fresh glucagon in FAFG and THCFG and glucagon after incubation for 3 days at 37° C. in FAFG and THCFG. A indicates the injection peak. B is the ferulic acid peak. C is the peak showing Met-27 oxidation.

Parent peak retention by HPLC following the United States Pharmacopeia (USP) monograph (http://www.uspbpep.com/usp29/v29240/usp29nf24s0_m35160.html; last accessed 4 Apr. 2014 and incorporated by reference herein) provides a measure of glucagon stability—the higher the percentage of parent peak that is retained, the less degradation (such as oxidation or deamidation) has occurred. FIG. 5 shows glucagon parent peak retention after aging FAFG and THCFG for 0 days (freshly formulated) and 3 days. Table 3 shows the results of performing high-pressure liquid chromatography as described above and analyzing the area under the curve for glucagon for the following formulations aged under the indicated conditions. Retention of glucagon in FAFC aged 7 days at 37° C. is 94% while retention of glucagon in THCFC aged 7 days at 37° C. is 91%.

HPLC reveals minor modification of glucagon, with some oxidation occurring in both FAFC and THCFC. It has been previously shown though that oxidation of glucagon does not inhibit bioactivity (Caputo et al *Peptides* 45, 40-47 (2013); incorporated by reference herein). When these formulations were aged at different temperatures for 4 weeks, they showed varying parent peak retentions, with FAFG at 4° C. storage producing the highest retention at 92% (Table 3).

TABLE 3

Stability of glucagon in formulations comprising ferulic acid or tetrahydrocurcumin:

| Number of days aged | Temp ° C. | BG | FAFG | THCFG |
|---|---|---|---|---|
| 0 | 20 | 100 | 100 | 100 |
| 7 | 37 | 96 | 94 | 91 |

Ferulic acid and tetrahydrocurcumin modify glucagon less than curcumin. For example, glucagon incubated with curcumin for 7 days at 37° C. results in complete oxidation of the glucagon. The addition of 1 mg/ml L-methionine to a curcumin formulation did result in a higher retention of unmodified glucagon but there were still other artifacts of peptide degradation.

Example 6

Figure 6A:
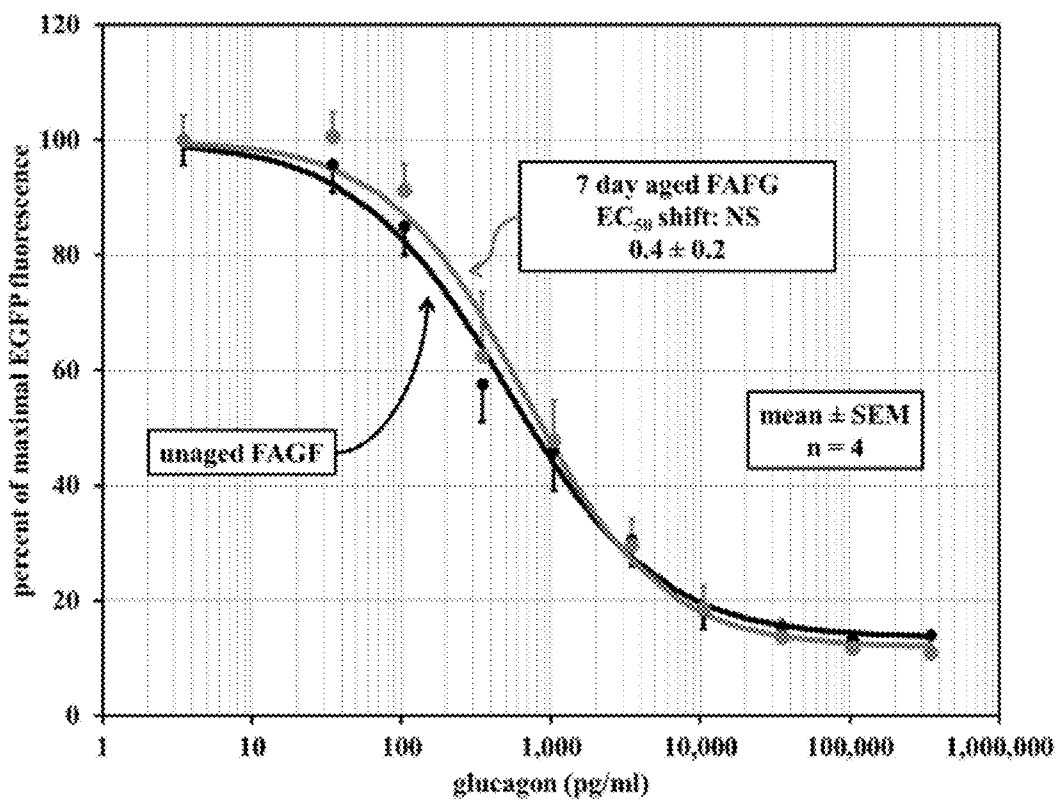
FIGS. 6A and 6B are dose response curves that depict glucagon potency retention of FAFG (6A) or THCFG (6B) after aging for 7 days at 37° C., wherein the potency shift is determined by the following formula.
Figure 6B:
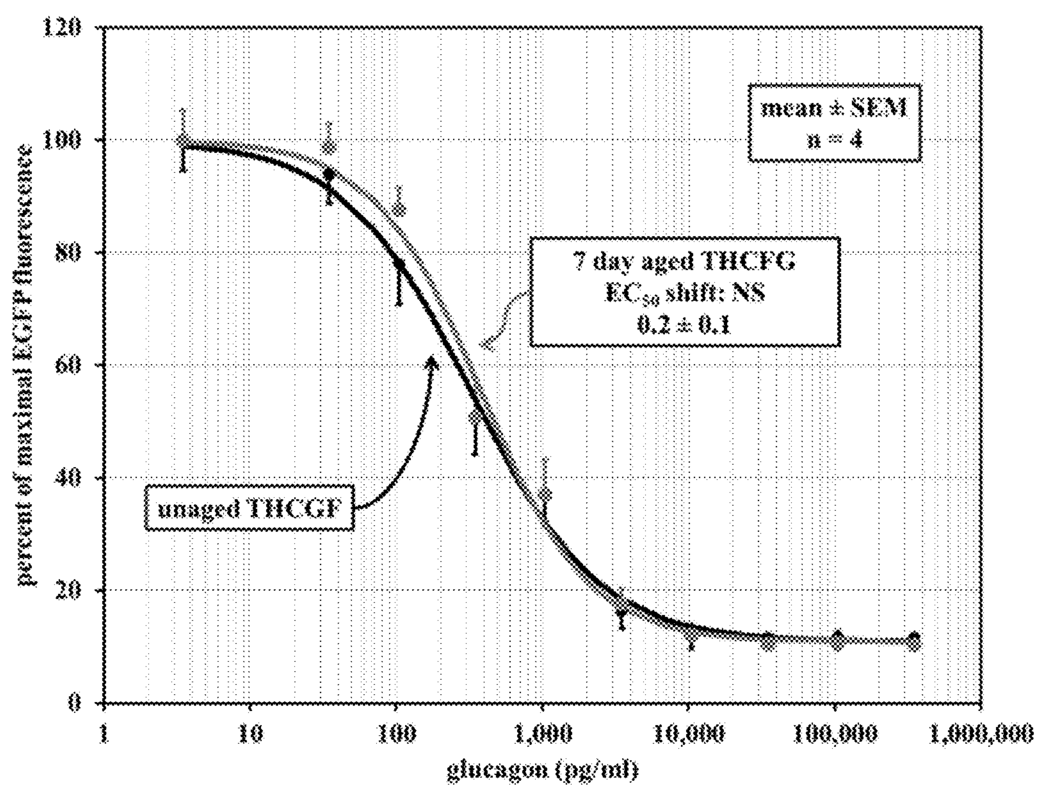

Formulations Comprising Ferulic Acid and Tetrahydrocurcumin Maintain the Potency of Aged Glucagon when Tested In Vitro Use of a eukaryotic cell based bioassay with a reporter molecule fused into the glucagon recognition pathway (Caputo et al, 2013 supra and Jackson M A et al, *Curr Diabetes Rep* 12, 705-710 (2012); incorporated by reference herein) allowed the determination that that aged FAFG or THCFG have the same potency as freshly made formulations. Results are shown in FIGS. 6A and 6B. This finding is consistent with what has been shown previously in the fact that oxidation of glucagon does not substantially affect potency Caputo et al, 2013 supra).

Example 7

Formulations Comprising Ferulic Acid Maintain the Potency of Aged Glucagon when Tested In Vivo A total of eight pigs each were given freshly formulated FAFG, FAFG aged 7 days at 37° C., and fresh buffered glucagon (BG) without excipients. Animals were anesthetized with isoflurane. The animals were injected with glucagon at time 0 and glucose was monitored every 10 minutes. Results are shown in FIG. 7.

A t-test with the Holm-Bonferroni correction for multiple comparisons showed no statistical difference of the pharmacodynamics of any of the three preparations (early time to half max, time to max effect, the maximal increase in glucose, and the AUC for increase in glucose).

The invention claimed is:

1. A liquid formulation comprising:
glucagon;
a buffer that maintains the formulation at a pH between pH 8.8 and 9.4;
and a curcumin derivative selected from ferulic acid or tetrahydrocurcumin.

2. The formulation of claim 1 comprising at least 1 mg/ml of glucagon.

3. The formulation of claim 1 comprising a glycine buffer.

4. The formulation of claim 3 comprising at least 80 mM glycine.

5. The formulation of claim 1 further comprising polysorbate-80.

6. The formulation of claim 5 comprising at least 0.5% v/v polysorbate-80.

7. The formulation of claim 1 further comprising albumin.

8. The formulation of claim 7 comprising at least 1.0 mg/ml human serum albumin.

9. The formulation of claim 1 further comprising L-methionine.

10. The formulation of claim 9 comprising ferulic acid and at least 0.1 mg/ml L-methionine.

11. The formulation of claim 9 comprising tetrahydrocurcumin further comprising at least 1.0 mg/ml L-methionine.

12. The formulation of claim 1 wherein the pH of the buffer is between 8.9 and 9.1.

* * * * *